(12) United States Patent
Hu

(10) Patent No.: US 9,963,751 B2
(45) Date of Patent: May 8, 2018

(54) COMPOSITIONS AND METHODS FOR IDENTIFYING AGENTS TO REDUCE HEPATITIS B VIRUS COVALENTLY CLOSED CIRCULAR DNA

(71) Applicant: THE PENN STATE RESEARCH FOUNDATION, University Park, PA (US)

(72) Inventor: Jianming Hu, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days. days.

(21) Appl. No.: 15/355,643

(22) Filed: Nov. 18, 2016

(65) Prior Publication Data

US 2017/0145521 A1    May 25, 2017

Related U.S. Application Data

(60) Provisional application No. 62/259,475, filed on Nov. 24, 2015.

(51) Int. Cl.

| A61K 39/00 | (2006.01) |
| C07K 14/005 | (2006.01) |
| C07K 14/03 | (2006.01) |
| C07K 14/125 | (2006.01) |
| C07K 14/18 | (2006.01) |
| C12Q 1/70 | (2006.01) |
| C12Q 1/68 | (2018.01) |

(52) U.S. Cl.
CPC ............ *C12Q 1/70* (2013.01); *C12Q 1/6816* (2013.01); *C12Q 1/706* (2013.01)

(58) Field of Classification Search
CPC ................. C07K 14/005; A61K 39/00; A61K 2039/5154; A61K 2039/5158; C12N 7/00
See application file for complete search history.

(56) References Cited

U.S. PATENT DOCUMENTS

| 6,610,471 | B1 | 8/2003 | Isom et al. |
| 2005/0153280 | A1 | 7/2005 | Shih |
| 2006/0234212 | A1 | 10/2006 | Bozdayi |
| 2007/0042356 | A1 | 2/2007 | Schildgen et al. |
| 2007/0048736 | A1 | 3/2007 | Chang et al. |
| 2007/0264284 | A1 | 11/2007 | Locarnini et al. |
| 2011/0015122 | A1 | 1/2011 | Zimmerman et al. |
| 2013/0011435 | A1 | 1/2013 | Martin et al. |
| 2015/0274652 | A1 | 10/2015 | Hartman |

FOREIGN PATENT DOCUMENTS

WO    2004009032    1/2004

OTHER PUBLICATIONS

Orabi, et al., An Aptamer against the Matrix Binding Domain on the Hepatitis B Virus Capsid Impairs Virion Formation, Journal of Virology, vol. 89, No. 18, pp. 9281-9287 Sep. 1, 2015.
Delaney, et al., Cross-Resistance Testing of Antihepadnaviral Compounds Using Novel Recombinant Baculoviruses Which Encode Drug-Resistant Strains of Hepatitis B Virus, Antimicrobial Agents and Chemotherapy, vol. 45, No. 6, pp. 1705-1713 Jun. 1, 2001.
Nursthorn, et al., Peginterferon Alpha-2b Plus Adefovir Induce Strong cccDNA Decline and HBsAg Reduction in Jatients With Chronic Hepatitis B, Hepatology, vol. 44, No. 3, pp. 675-684 Sep. 1, 2006.
De Masson, et al., Identification of CD245 as myosin 18A, a receptor for surfactant A: A novel pathway for activating human NK lymphocytes, Oncoimmunology, vol. 5, No. 5, e1127493, 11 pages Mar. 1, 2016.
Cui, et al., Alteration of Mature Nucleocapsid and Enhancement of Covalently Closed Circular DNA Formation by Hepatitis B Virus Core Mutants Defective in Complete-Virion Formation, Journal of Virology, vol. 89, No. 19, pp. 10064-10072, Jul. 22, 2015.

*Primary Examiner* — Barry A Chestnut
(74) *Attorney, Agent, or Firm* — Hodgson Russ LLP

(57) ABSTRACT

Provided are compositions and methods for identifying test agents as candidate for use in reducing hepatitis B virus (HBV). The methods involve a) introducing at least one test agent into mammalian cells, the cells having one or more plasmids that encode an HBV genome, wherein the genome includes a segment encoding a mutated HBV core (HBc), wherein the HBc mutation is L60A, I126A, K96A or a combination thereof. The test agent is allowed to be in contact with the mammalian cells for a period of time. Subsequently, amounts of HBV cccDNA in the mammalian cells are determined. The method can be performed in vitro or in vivo. A reduction in cccDNA relative to a control indicates the test agent in the test container is a candidate for reducing HBV in an individual. Cell cultures divided into reaction containers that each contain a distinct test agent are also included.

8 Claims, 7 Drawing Sheets

Figure 1:
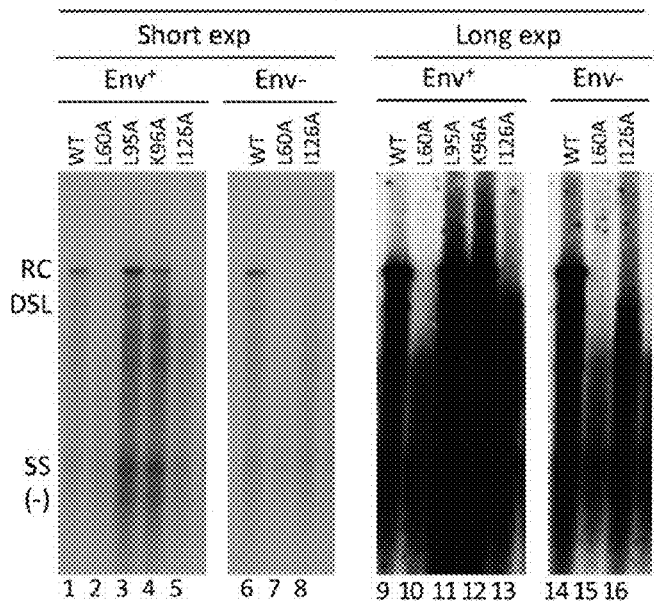
Figure 1:
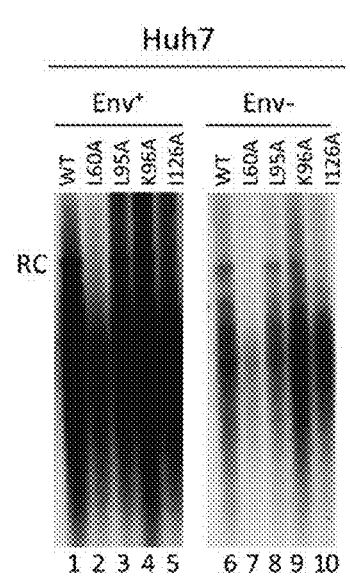

SEQUENCE LISTING

<160> NUMBER OF SEQ ID NOS: 1

<210> SEQ ID NO 1
<211> LENGTH: 183
<212> TYPE: PRT
<213> ORGANISM: HEPATITIS B VIRUS

<400> SEQUENCE: 1

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Pro Gln Cys
            180
```

COMPOSITIONS AND METHODS FOR IDENTIFYING AGENTS TO REDUCE HEPATITIS B VIRUS COVALENTLY CLOSED CIRCULAR DNA

CROSS REFERENCE TO RELATED APPLICATIONS

This application claims priority to U.S. provisional application Ser. No. 62/259,475, filed on Nov. 24, 2015, the disclosure of which is incorporated herein by reference.

STATEMENT REGARDING FEDERALLY SPONSORED RESEARCH

This invention was made with government support under contract no. R01 AI074982 awarded by the National Institutes of Health. The government has certain rights in the invention.

FIELD

The present invention relates generally to Hepatitis B Virus (HBV) infection and more particularly to identifying agents that can target HBV covalently closed circular (CCC) DNA.

BACKGROUND

The human pathogen hepatitis B virus (HBV) belongs to the family of Hepadnaviridae, a group of small, hepatotropic DNA viruses that also include closely related animal viruses, such as the duck hepatitis B virus (DHBV). Hepadnaviruses contain a small (ca. 3-kb), partially double-stranded (ds-), relaxed circular (rc) DNA genome enclosed within an icosahedral capsid that is, in turn, formed by multiple copies (240 or 180) of the viral capsid or core protein. All hepadnaviruses replicate their genomic DNA via an RNA intermediate, termed the pregenomic RNA (pgRNA), by reverse transcription. Upon entering the host cells, the virion rcDNA is released into the nucleus for conversion into a covalently closed circular (ccc) DNA, which then serves as the viral transcriptional template for the synthesis of all viral RNAs, including pgRNA, by the host RNA polymerase II. After being packaged together with the viral reverse transcriptase (RT) protein into assembling immature nucleocapsid (NC), the pgRNA is converted by the multifunctional RT, first to a single-stranded DNA (ssDNA) and then to the characteristic rcDNA. The mature (i.e., rcDNA-containing) NCs are then encapsulated by the viral envelop proteins and secreted extracellularly as virions, or they can deliver their rcDNA content to the nucleus to be converted to more cccDNA via an intracellular cccDNA amplification pathway.

The HBV core protein (HBc) consists of two separate domains: the N-terminal domain (NTD), which is sufficient to form the capsid shell, and the C-terminal domain (CTD), which is dispensable for capsid assembly but nevertheless essential for viral replication. The CTD is highly basic and dynamically phosphorylated, which is thought to be important for viral RNA packaging and DNA synthesis. The NTD has also been shown to play a role in viral DNA synthesis beyond its role in capsid assembly.

The two alternative fates of mature NCs (i.e., envelopment versus cccDNA amplification) are known to be regulated by the viral envelope proteins. Since HBc forms the NC shell, it is also likely to play a key role in these processes. On the other hand, the HBc CTD harbors the nuclear localization signal (NLS) and thus is thought to play an important role in delivering the rcDNA in mature NCs to the nucleus for cccDNA formation. Since at least partial disassembly (uncoating) of the mature NCs is required to allow rcDNA release to the host cell nucleus for cccDNA formation, NC stability or integrity likely plays a critical role in cccDNA formation. In established human hepatoma cells in culture, which have limited ability to support HBV cccDNA formation, a processed form of rcDNA called protein-free (PF) or deproteinated (dp) rcDNA, also accumulates to high levels. PF-rcDNA is derived from rcDNA, but the viral RT protein, which is used as a protein primer to initiate viral DNA synthesis and remains attached to rcDNA in mature NCs, has been removed. At least partial uncoating of the mature NCs is also thought to be required for the removal of RT from rcDNA and the generation of the PF-rcDNA. Thus, regardless of whether PF-rcDNA is a true intermediate during the conversion of RC to cccDNA, it may be a useful marker for the uncoating of mature NCs. There is an ongoing need for improved approaches that are suitable for analyzing the effect of multiple test agents on the role of HBc in coordinating the two alternative fates of mature NCs, and how or if the formation of cccDNA can be manipulated for use in prophylaxis and/or therapy of HBV. The present disclosure is pertinent to this need.

SUMMARY OF THE INVENTION

This disclosure relates to methods for identifying test agents as candidate for use in reducing hepatitis B virus (HBV). In one aspect a method of the disclosure generally comprises: a) introducing at least one test agent into a mammalian cell culture comprising mammalian cells, the cells comprising one or more plasmids that encode an HBV genome, wherein the genome comprises a segment encoding a mutated HBV core (HBc), wherein the HBc mutation is L60A, I126A, K96A or a combination thereof. The test agent is allowed to be in contact with the mammalian cells for a period of time. Subsequently, amounts of HBV cccDNA in the mammalian cells is determined. A reduction in cccDNA relative to a control indicates the test agent in the test container is a candidate for reducing HBV in an individual. The method is suitable in certain approaches for concurrently screening multiple test agents, such as by dividing cell cultures into separate reaction containers and adding a distinct test agent to the separate containers. In certain implementations the control comprises a cccDNA value produced by a control mammalian cell culture comprising one or more plasmids that encode an HBV that does not comprise any of the L60A, I126A, K96A mutations, or comprises different mutations than in the test experiments. The disclosure includes mammalian cell cultures that comprise the aforementioned plasmid(s), wherein the mammalian cells of the cell culture are divided into a plurality of reaction containers, and wherein the plurality of reaction containers each contains a distinct test agent.

The disclosure also provides a method for screening test agents that generally comprises: a) introducing into a non-human mammalian subject a vector encoding an HBV genome, wherein the genome comprises a segment encoding a mutated HBV core (HBc) protein, wherein the HBc mutation is L60A, I126A, K96A, or a combination thereof; b) introducing into the mammalian subject a test agent, and subsequently, c) determining amounts of HBV cccDNA in the cells of the mammal, wherein a reduction in cccDNA in the cells relative to a control indicates the test agent is a candidate for use in reducing HBV in an individual. The disclosure also provides a method for identifying an inhibitor of covalently closed circular (CCC) DNA production, the method comprising a) contacting a test agent with a mutated HBV core (HBc) protein comprising an HBc mutation that is L60A, I126A, K96A or a combination thereof, wherein the HBc is present in mammalian cells; b) allowing the test agent to be in contact with the HBc for a period of time, and subsequently, c) determining conversion of relaxed circular (rc) rcDNA to cccDNA, wherein a reduction in conversion of rcDNA to cccDNA relative to a control identifies the test agent as an inhibitor of the cccDNA production.

DESCRIPTION OF THE FIGURES

FIG. 1. Analysis of NC-associated HBV DNA extracted following exogenous nuclease digestion. HBV-replicating plasmids expressing the WT or the indicated HBc mutants were transfected into HepG2 (A) or Huh7 (B) cells. HBV NC-associated DNA (core DNA) was isolated from cytoplasmic lysate of transfected cells following removal of the transfected plasmids by MNase digestion and analyzed by Southern blotting using a viral DNA probe. "Env+" or "Env−" denotes that the HBV envelope proteins were expressed or not expressed by the transfected plasmids. SS, single-stranded [(−)-strand] DNA. Lanes 9 to 16 in panel A represent a longer exposure (exp) of the same samples shown in lanes 1 to 8.

FIG. 2 Strand-specific analysis of NC-associated HBV DNA extracted following exogenous nuclease digestion. The same HBV core DNA samples from FIG. 1—all from replication constructs expressing the envelope proteins (Env+) (HepG2 cells in FIG. 1A, lanes 1 to 5, and Huh7 cells in FIG. 1B, lanes 1 to 5) were heat denatured first and then analyzed by Southern blotting using a strand-specific RNA probe to detect the (−)-strand (A, lanes 1 to 5; B, lanes 1 to 5, 11, and 12) or (+)-strand viral DNA (A and B, lanes 6 to 10). FL, full-length (−)- or (+)-strand DNA. Lanes 11 to 12 in panel B represent a longer exposure of the same samples shown in lanes 1 and 2.

FIG. 3 Analysis of HBV NC assembly and RNA packaging. The same HBV-replicating plasmids as in FIG. 1 were transfected into HepG2 (A) or Huh7 (B) cells. HBV NCs from cytoplasmic lysate of transfected cells were resolved by native agarose gel electrophoresis and transferred to nitrocellulose membrane. The NC-associated RNA was detected by an HBV-specific riboprobe (top), and the capsids were detected by an anti-HBc antibody (bottom).

FIG. 4 Analysis of HBV PF DNA. HBV-replicating plasmids as in FIG. 1 were transfected into HepG2 cells. PF DNA was extracted and analyzed by Southern blotting, using an HBV-specific DNA probe (A and D) or a (−)-strand-specific (B) or (+)-strand-specific (C) RNA probe. Plasmid DNA copurifying with the PF HBV DNA was degraded by DpnI digestion as described in Materials and Methods. The plasmid fragments are indicated (A). Following DpnI digestion, the DNA was further denatured by boiling before analysis (B and C) or boiling followed by EcoRI digestion (D). SS, single-stranded [full-length (−)- or (+)-strand] DNA derived from the denatured PF-RC and PF-DSL DNA; CCC/E1, cccDNA linearized by EcoRI digestion.

FIG. 5 Analysis of NC-associated HBV DNA extracted without exogenous nuclease digestion. HBV-replicating plasmids (all in the Env− background) expressing the WT or the indicated HBc mutants were transfected into HepG2 cells. HBV NC-associated DNA (core DNA) was released from cytoplasmic lysate of transfected cells, without the MNase digestion step, by SDS-proteinase K digestion and analyzed by Southern blotting using an HBV DNA probe. Lanes 6 and 7 represent a longer exposure of lanes 1 and 2. SS, single-stranded [full-length (−)-strand] DNA.

FIG. 6 Analysis of HBV NCs by EPR. The HBV-replicating plasmid expressing the WT (lanes 1 to 3) or I126A mutant (lanes 4 to 6) HBc was transfected into HepG2 cells. Cytoplasmic lysate of transfected cells was treated with MNase and then used in EPR in vitro (lanes 2, 3, 5, and 6) or not (lanes 1 and 4). Following EPR, a portion of the reaction mixtures was treated with DNase 1 (1 mg/ml) (lanes 3 and 6). HBV core DNA was then released from NCs by SDS-proteinase K digestion and analyzed by Southern blotting using air HBV DNA probe. An HBV DNA-containing plasmid was included as a control to verify the efficacy of DNase digestion following EPR. SS, single-stranded [full-length (−)-strand] DNA.

FIG. 7 Location of the HBc residues mapped onto the three-dimensional structure of an HBc dimer. The L60, L95, K96, and I126 positions analyzed here, as well as the V124, which are highlighted in dark gray.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure provides compositions and methods for identifying agents as candidates for use in prophylaxis and/or therapy of HBV infection. The disclosure includes the following non-limiting aspects.

In one approach, the disclosure provides a method for screening a plurality of test agents to determine if they are candidates for use in reducing HBV in an individual. In general, the method comprises analyzing test agents using any system wherein the conversion of cccDNA using particular mutants described herein is performed.

In one embodiment, the method comprises screening a plurality of test agents to identify candidates for use in reducing HBV in an individual by: a) contacting a plurality of distinct test agents with mutated HBV core (HBc) protein comprising an HBc mutation that is L60A, I126A, K96A or a combination thereof; b) allowing the test agent to be in contact with the HBc protein for a period of time, and subsequently, c) determining conversion of rcDNA to cccDNA, wherein a reduction in cccDNA relative to a control indicates the test agent is a candidate for use in reducing HBV in an individual.

In one embodiment, the disclosure comprises a) introducing a plurality of distinct test agents into separate test containers, each test container comprising mammalian cells which comprise one or more plasmids that encode an HBV genome, wherein the genome comprises a segment encoding a mutated HBV core (HBc) protein, wherein the HBc mutation is L60A, I126A, K96A or a combination thereof;

b) allowing the test agent to be in contact with the mammalian cells for a period of time, and subsequently c) determining amounts of HBV cccDNA in the mammalian cells in each test container, wherein a reduction in cccDNA relative to a control indicates the test agent in the test container is a candidate for reducing HBV in an individual.

In another aspect the disclosure comprises a method for screening test agent comprising:

a) introducing into a non-human mammalian subject a vector encoding an HBV genome, wherein the genome comprises a segment encoding a mutated HBV core (HBc) protein, wherein the HBc mutation is L60A, I126A, K96A, or a combination thereof;

b) introducing into the mammalian subject a test agent, and subsequently c) determining amounts of HBV cccDNA in the cells of the mammal, wherein a reduction in cccDNA in the cells relative to a control indicates the test agent is a candidate for use in reducing HBV in an individual. In one embodiment, the cells of the animal are liver cells.

In another aspect the disclosure provides a transgenic non-human mammal and a method of using it for screening test agents for use in prophylaxis and/or therapy of HBV infection, where the transgenic non-human mammal is engineered to express a mutated HBc protein, wherein the HBc mutation is L60A, I126A, K96A, or a combination thereof. The method comprises administering to the non-human mammal a test agent and determining cccDNA in a sample obtained from the mammal, wherein a reduction in cccDNA indicates that test agent is a candidate for use in reducing HBV in an individual. In one embodiment, PF-rcDNA is measured instead of cccDNA. In certain aspects PF-rcDNA comprises evidence of rcDNA processing and thus serves a putative intermediate during RC to cccDNA conversion. Accordingly, in embodiments, determining PF-rcDNA comprises determining cccDNA.

The amino acid sequence of HBc is known in the art and the location of the mutations disclosed herein is taken in reference to it. In an embodiment wild type HBc comprises or consists of the sequence:

```
                                            (SEQ ID NO: 1)
MDIDPYKEFGATVELLSFLPSDFFPSVRDLLDTASALYREALESPEHCSP

HHTALRQAILCWGELMTLATWVGNNLEDPASRDLVVNYVNTNMGLKIRQL

LWFHISCLTFGRETVLEYLVSFGVWIRTPPAYRPPNAPILSTLPETTVVR

RRGRSPRRRTPSPRRRRSQSPRRRRSQSREPQC.
```

The disclosure includes all nucleotide sequences encoding HBc each mutant alone, and every combination of the mutants. Thus, the disclosure includes methods relating to use of polynucleotides encoding HBc with the L60A mutation alone, the I126A mutation alone, the K96A mutation alone, a combination of all three mutations, and a combination of the L60A and I126A mutations, a combination of the L60A and K96A mutations, and a combination of the I126A and K96A mutations. Use of HBc polypeptides comprising these mutations and combinations thereof are included in the disclosure. Use of cell cultures and cell lines comprising expression vectors encoding the HBc mutant polypeptides, and non-human animals engineered to express the HBc mutant polypeptides either episomally or by integration into the genome, are also included in this disclosure, as described further below.

Test agents identified using compositions and methods of this disclosure will have relevance to human and non-human animals. In certain embodiments, compounds identified using the compositions and methods of will be useful for, among other purposes, inhibiting reproduction and/or growth of HBV, and/or for prophylaxis and/or therapy for disorders that are correlated with HBV infection. Thus, the present disclosure relates to a system to identify agents that can be used in pharmaceutical approaches to treating HBV infection that will be suitable for human and veterinary uses.

In general, this disclosure provides approaches which include but are not limited to making and using single-celled or multi-cellular eukaryotic organisms as a system to express and analyze the function of test agents by introducing into the organisms a polynucleotide encoding one or a combination of the HBc mutants described herein. In embodiments the polynucleotide comprises an expression vector. Any expression vector can be used and will be dependent upon the type of expression system (i.e., the type of cells) that are used and can be selected by one skilled in the art, given the benefit of the present disclosure. In embodiments, the expression vector comprises a plasmid or a viral vector. Polynucleotides encoding the HBc mutants may be maintained as episomal elements, or they may be transiently or stably integrated into a chromosome of any particular eukaryotic cell. In embodiments, expression of the HBc mutants is constitutive, or is conditional, such as use of a cell-specific or tissue-specific promoter, or an inducible promoter to drive expression of the HBc mutants.

In certain embodiments, the HBc mutant is encoded on a single expression vector which does not encode all, or only encodes some, of the other HBV proteins (non HBc proteins) that are required for HBV expression. Such proteins are well known in the art. In other embodiments, the HBc mutant is encoded by the same expression vector that also encodes all of the other HBV components required for HBV expression. In embodiments, the HBV proteins are encoded by four open reading frames (ORFs) that are translated into viral core protein, surface proteins, polymerase/reverse transcriptase, and HBx. Thus, in embodiments the one or more vectors encode all or some of the mutant HBc, HBs, HBV polymerase, and HBx.

In another approach a polynucleotide encoding any of the HBc mutants (and additional HBV proteins if desired) can be integrated into the chromosome(s) of a non-human mammal. Methods of integrating polynucleotides into chromosomes are known in the art and include approaches such as homologous recombination of any polynucleotide of interest into chromosomes of, for example, embryonic stem cells, such that a transgenic mammal can be developed using established techniques as described further below. In certain embodiments, the disclosure includes a transgenic mammal wherein an HBc mutant polypeptide is expressed at least in the liver of the mammal.

For ease of reference, cells engineered to express an HBc mutant according to the method of the invention are from time to time referred to herein as "HBc mutant+" cells.

In one embodiment, the method comprises providing a plurality of distinct samples comprising HBc mutant+ cells. In one embodiment, each sample expresses the same HBc mutant or mutant combination. In alternative embodiments, some or all of the samples express a different HBc mutant, or a different combination of mutants. The plurality of HBc mutant+ cell samples is configured so as to be amenable for high throughput screening (HTS). In certain embodiments, the samples are divided into a plurality of reaction chambers, such as wells in a plate. Any multi-well plate or other container can be used. In certain approaches, one or more 384-wells plates are used.

The method includes exposing each HBc mutant+ cell sample to at least one test agent, allowing a period of time for the test agent to be in contact with the HBc mutant+ cell samples, and subsequently determining HBV cccDNA, wherein a reduction in HBV cccDNA is indicative that the test agent is a candidate for use in prophylaxis and/or therapy of HBV infection.

cccDNA can be assessed using any suitable approach. The current gold standard for detection of cccDNA is Southern blot analysis following resolution of cccDNA on an agarose gel, which clearly separates cccDNA from the other viral DNA species such as rcDNA. Additionally, the identity of cccDNA can be further verified by its resistance to heat denaturation and linearization following a single cut restriction digestion (see for example, *Formation of hepatitis B virus covalently closed circular DNA: removal of genome-linked protein.* J Virol 81:6164-6174)). For clinical/tissue samples that may contain few infected cells and thus very low levels of cccDNA an amplification process is preferred to detect the low levels of cccDNA. Relatively selective amplification strategies for sensitive detection of cccDNA via PCR or rolling circle amplification (RCA) have been developed and can be used in quantification of low levels of cccDNA normally found in tissue samples, as described further below.

In certain embodiments, PCR-based approaches can be used, including but not necessarily limited to nested PCR reactions with suitable primers. In embodiments, primers spanning across the gap in the minus strand and primers corresponding to the variable region on the plus strand can be used to amplify non-interrupted cccDNA. In particular, quantitative measurement of HBV cccDNA may occur wherein in an HBV genome, the incomplete plus strand has a variable 3' end but there is a defined 5' end around position 1600 near direct repeat 2 (DR2), while the complete minus strand has defined 5' and 3' ends with a terminal redundancy of 9 bases. There is a gap near position 1800 near direct DR1. Therefore, primers can be designed and used to specifically amplify DNA fragments from replication intermediate cccDNA, but not from viral genome DNA, by taking advantage of sequence and structural differences between the viral genome and cccDNA. In one approach an RT-PCR technique is used, such as that described in U.S. patent publication no. 20040058314 from which the description of reagents and methods for detecting and quantifying HBV cccDNA is incorporated herein by reference. In certain approaches the disclosure involves use of RCA to selectively amplify circular DNA, which may then be further amplified and quantified. In some examples, a sample comprising the cccDNA can be processed using one or more nucleases to selectively digest rcDNA, replicative dsDNA and ssDNA. In embodiments, the so-called "Invader Assay" can be used (see, for example, Kwiatkowski R W, et al., Clinical, genetic and pharmacogenetic applications of the Invader assay. Mol. Diagn. 1999. 4:353-364). In embodiments a droplet digital polymerase chain reaction can be used (see, for example, Mu, D., et al. A sensitive and accurate quantification method for the detection of hepatitis B virus covalently closed circular DNA by the application of a droplet digital polymerase chain reaction amplification system. Biotechnology Letters. October 2015, Volume 37, Issue 10, pp 2063-2073). In embodiments, real-time PCR can be used (see, for example, Takkenberg, et al. Validation of a sensitive and specific real-time PCR for detection and quantitation of hepatitis B virus covalently closed circular DNA in plasma of chronic hepatitis B patients. J Med Virol. 2009 June; 81(6):988-95.) In embodiments, cccDNA can be detected and amounts determined by electrophoretic techniques which allow separation and detection of cccDNA. (See, for example, Cai, et al., A Southern Blot Assay for Detection of Hepatitis B Virus Covalently Closed Circular DNA from Cell Cultures, Methods in Molecular Biology, Volume: 1030 (2013) pgs 151-161). In certain embodiments, cccDNA is detected as generally described herein for FIG. 4, and/or as described in Gao W, Hu J. 2007. *Formation of hepatitis B virus covalently closed circular DNA: removal of genome-linked protein.* J Virol 81:6164-6174, from which the description of obtaining and detecting cccDNA and differentiating cccDNA from other HBV polynucleotides is incorporated herein by reference.

For the animal models described herein, a biological sample can be obtained from the animal model and tested directly, or it can be subjected to one or more processing steps to, for example, isolate particular cell types or tissue types. In certain embodiments the biological sample is a liquid biological sample, such as blood, plasma, or urine. In other embodiments the sample comprises a biopsy. In certain approaches cccDNA can be detected in situ using at least in part tissue samples, such as tissue sections embedded in a substrate, such as a paraffin-embedded tissue. cccDNA can also be extracted from the tissue sections, or liver tissue biopsy or autopsy and quantified using any suitable approach.

In embodiments, the effect of a test agent on cccDNA in a cell culture can be compared to a reference. Any suitable control can be used as a reference, including but not limited to a cell culture to which a test agent has not been added, or to which an agent with a known effect on cccDNA is added, or the reference can be a standardized reference, such as a known value that relates to HBV replication and/or cccDNA levels. In embodiments, the reference is a positive control, or a negative control. In embodiments, the reference is an amount of cccDNA that is produced by a control, i.e., a wild type HBc.

With respect to non-human mammals that are encompassed by the present disclosure, it includes transient and non-transient introduction of a polynucleotide encoding an HBc mutant into cells, wherein the polynucleotide is maintained episomally, or is integrated into a chromosome of the mammal.

In certain approaches, polynucleotides can be introduced into neonatal or adult mice via injection into certain tissues such as the liver, using modified retroviral approaches, or by hydrodynamic gene delivery. Each of these approaches is well known in the art and can be readily adapted for use with the present disclosure. In certain embodiments the polynucleotides are introduced into the liver only, or are selectively expressed in the liver only, such as by being linked to a promoter that is only operative in hepatic cells.

In another aspect the disclosure comprises making and using transgenic mammals, such as mice, wherein a polynucleotide encoding an HBc mutant is introduced into at least one chromosome of a mouse. Compositions and methods for making homologous replacements of genes (i.e., gene knockins) in mice are well known in the art, and can be adapted for use with the present disclosure using any vector that is suitable for creating murine embryonic stem cells (ES). In embodiments, the polynucleotide can be integrated randomly into a chromosome of an ES cell, or a targeted insertion using a vector for recombination between homologous sequences can be used. As such, the vector is adapted to facilitate homologous recombination with a segment of murine chromosome. In general, a vector that is adapted for use in homologous combination with a target site in a recipient chromosome will have features known to those skilled in the art. These features include but are not necessarily limited to a selectable marker, such as the well characterized Neo marker, polycloning sites into which the HBc mutant gene segment is cloned as well as for inserting gene segments that are the same as those in the targeted portion of the chromosome so that the replacement is targeted correctly, a site for linearization of the vector, sites which are recognized by enzymes involved in certain recombination events, such as LoxP sites, and promoter sequences.

In one approach, ES can be obtained using routine techniques and are chosen for their ability to integrate into and become part of the germ line of a developing embryo so as to create germ line transmission of the transgene. Thus, any ES cell or cell line that can do so is suitable for use in the invention. Introduction of a vector described herein into ES cells may be accomplished using a variety of methods well-known in the art, including, for example, electroporation, microinjection, and calcium phosphate treatment. For introduction of the chosen DNA sequence, the targeting vector is added to the ES cells under appropriate conditions for the insertion method chosen. For example, if the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockin construct. Screening for cells which contain the transgene (e.g., homologous recombinants) may be done using a variety of methods, such as by screening with specific probes or by polymerase chain reaction (PCR), or by Southern blotting. Once selected, ES cells are injected into a blastocyst of an animal (e.g., a mouse) to form aggregation chimeras. A chimeric embryo can then be implanted into a suitable pseudopregnant female foster animal and the embryo brought to term to create a transgenic animal. Progeny harboring the homologously recombined DNA in their germ cells can be identified by standard techniques and used to breed animals in which all cells of the animal contain the homologously recombined DNA. Similar techniques can be adapted for testing any non-human mammals, including but not necessarily limited to pigs.

It will be apparent from the foregoing that the disclosure includes making any of several types of genetically modified non-human mammals that express a mutant HBc of this disclosure, and any such mammal can be tested for candidate agents according to the method of the invention. In order to test candidate agents for use in anti-HBV applications, the test agents can be administered to such an animal, and a biological sample obtained from the mammal can be tested to determine if administering the agent reduced cccDNA. The test agent can be administered to modified mammal via any suitable route, including but not limited to parenteral, subcutaneous, intraperitoneal, intrapulmonary, and intranasal approaches. Parenteral infusions include intramuscular, intravenous, intra-arterial, intraperitoneal, pulmonary instillation as mist or nebulization, and subcutaneous administration. The test agent could also be introduced as a component of a food or drinking item. More than one animal can be used to test distinct agents, and in certain embodiments, more than one agent can be tested in any particular animal.

The test agents can be administered in any form, including alone, or as a component of a composition of matter, such as a pharmaceutical formulation, and can be provided in liquid, solid, and semi-solid forms, tablets, capsules, granules, as a component of a feed, etc.

In certain embodiments, the plurality of test agents do not include sulfonamide compounds. In certain embodiments, the disclosure does not include determining secreted HBV e antigen, or any other potential surrogate for determining cccDNA. In certain embodiments, the disclosure includes comparing the effect of the one or more test agents to any suitable reference. The reference can be, for example, a control mammal that does not have HBV, or a mammal that does have HBV but is not given the test agent, or it can be a known value or range of values, or may be a value or range of values determined from analysis of a cohort of subjects. In embodiments, the reference comprises a statistical value, such as an area under a curve, or another area or plot on a graph, obtained from repeated measurements of cccDNA or a suitable alternative.

The disclosure includes fixing the results from analyzing test agents in a tangible medium, such as a computer file, and further comprises making a database of test results from analysis of a plurality of test agents. Such databases are also included in the scope of this disclosure. Thus, in embodiments, the disclosure includes a database or other compilation of results fixed in a tangible medium that comprises analysis of a plurality of test agents that can reduce HBV cccDNA, and an indication of test agents that are candidates for treating human HBV infection as determined using any method described herein. In embodiments, the databased comprises results obtained from testing more than 10, more than 100, or more than a 1,000 test agents.

The following specific examples are provided to illustrate the invention, but are not intended to be limiting in any way.

Example 1

This Example demonstrates that some but not all secretion-defective core NTD mutants accumulated little to no mature rcDNA. Previously, a number of HBc NTD mutations were shown to block secretion of DNA-containing virions. These mutations still allowed the synthesis of mature HBV rcDNA in vitro in the endogenous polymerase assay. To analyze the potential effects of the HBc mutants on reverse transcription and cccDNA synthesis inside the cells, we transfected HepG2 and Huh7 cells with HBV-replicating constructs harboring these NTD mutations. Two versions of these constructs were used, either with or without the expression of the viral envelope proteins, which are known to regulate cccDNA formation (Gao W, Hu J. 2007. Formation of hepatitis B virus covalently closed circular DNA: removal of genome-linked protein. J Virol 81:6164-6174; Summers J, Smith P M, Horwich A L. 1990. Hepadnavirus envelope proteins regulate covalently closed circular DNA amplification. J Virol 64:2819-2824; Lentz T B, Loeb D D. 2011. Roles of the envelope proteins in the amplification of covalently closed circular DNA and completion of synthesis of the plus-strand DNA in hepatitis B virus. J Virol 85:11916-11927). We found that in both cell lines, either with or without expression of the envelope proteins, the L95A and K96A mutants showed a core DNA (i.e., NC-associated DNA) pattern similar to that of the WT (FIG. 1 and Table 1).

TABLE 1

Relative levels of HBV DNA species accumulated by WT and mutant NCs

| | | Relative level of DNA species[a]: | | | | | |
|---|---|---|---|---|---|---|---|
| | | With MNase | | | Without MNase | | |
| Envelope | Core | Core RC/SS | PF-RC/core RC | CCC/core RC | Core RC/SS | PF-RC/core RC | CCC/core RC |
| WT | WT | 1.0 | 1.0 | 1.0 | 1.0 | 1.0 | 1.0 |
| | L60A | — | High | High | ≤0.2[b] | ≥3.6 | ≥3.9 |
| | L95A | 0.8 | 1.8 | 0.9 | 1.2 | 1.1 | 0.8 |
| | K96A | 0.4 | 4.3 | 4.9 | 0.9 | 2.3 | 3.3 |
| | I126A | — | High | High | 0.4 | 4.2 | 12.8 |
| Defective | WT | 1.0 | 1.0 | 1.0 | 1.0 | 1.0 | 1.0 |
| | L60A | — | High | High | ≤0.2[b] | ≥2.6 | ≥2.4 |
| | I126A | — | High | High | 0.3 | 3.7 | 7.8 |

[a]Reported as the ratio of the indicated viral DNA species normalized to that obtained with the WT NC, which is set as 1.0. Average values from multiple experiments are shown. The signal of a particular DNA species (e.g., core RC DNA) from the HBc mutants was normalized first to that of the corresponding DNA species from the WT analyzed on the same gel. The normalized values were then used to calculate the ratios of the different DNA species shown. Note that for the L60A and I126A HBc mutants, no RC DNA could be detected when MNase was used (indicated by "—"). Therefore, the exact ratios of PF-RC DNA or CCC DNA to core RC DNA in those cases could not be calculated but were much higher than those of the WT ("high").
[b]Due to the very small amounts of core RC DNA detected from the L60A mutant even in the absence of MNase digestion, this value might be an overrepresentation. Therefore, the ratios of PF-RC DNA or CCC DNA to core RC DNA in those cases represent only the minima.

Figure 2:
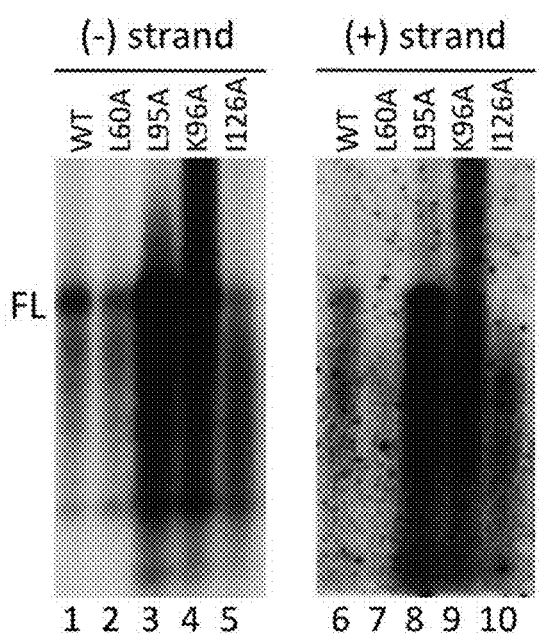
Figure 2:
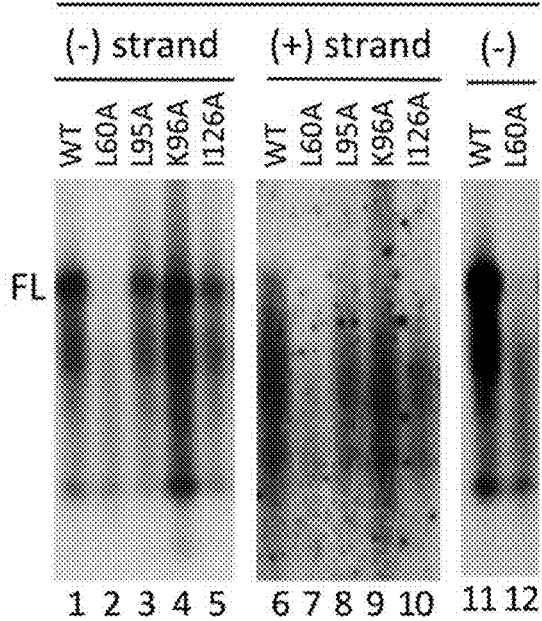
Figure 3:
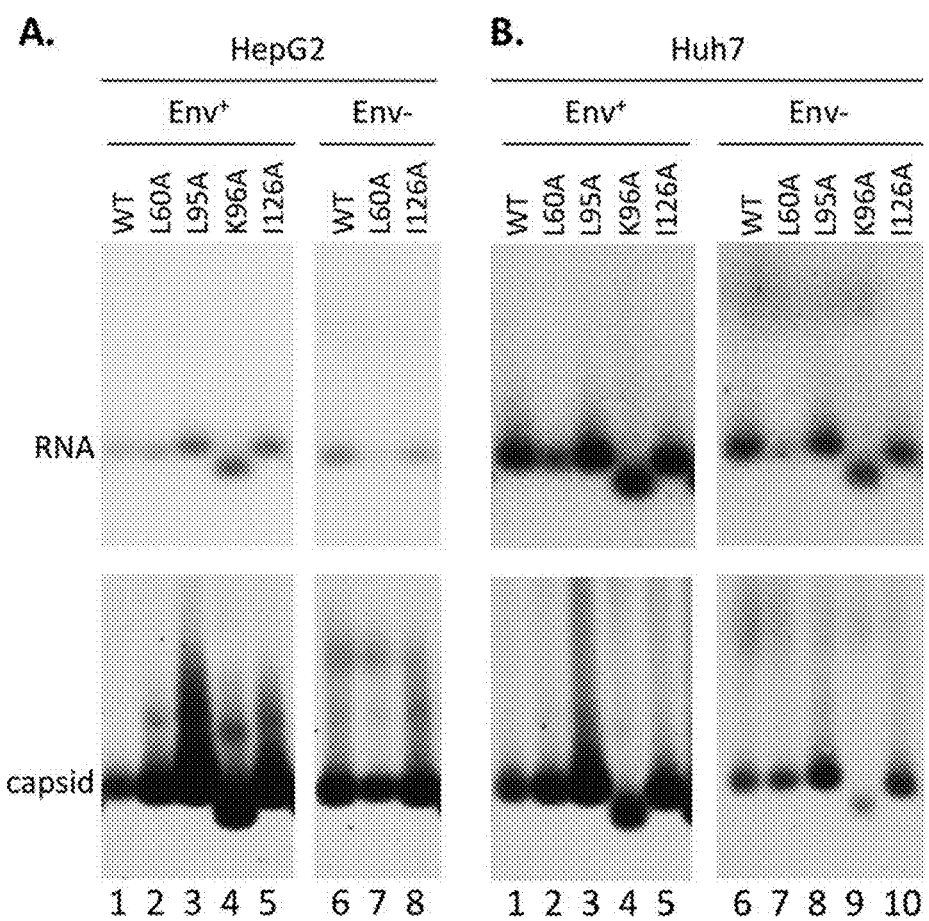

However, L60A and I126A mutants accumulated no detectable mature rcDNA. The minor form of mature DNA, the double-stranded linear (DSL) DNA (Staprans S, Loeb D D, Ganem D. 1991. Mutations affecting hepadnavirus plus-strand DNA synthesis dissociate primer cleavage from translocation and reveal the origin of linear viral DNA. J Virol 65:1255-1262), was affected the same way by the core mutations as rcDNA. All of these mutants made the ssDNA and immature dsDNA (FIG. 1). To further analyze the lengths of the viral minus-strand [(−)-strand] DNA and plus-strand [(+)-strand] DNA separately, the core DNA was first denatured before analysis. From the analysis of the native core DNA, the WT and all HBc mutants made full-length (−)-strand DNA (FIG. 2). The level of full-length (−)-strand DNA as well as the incomplete (−)-strand DNA made by the L60A mutant in the HepG2 cells (in the Env− background) (FIG. 1A, lanes 7 and 15) or in Huh7 cells (in both the Env+ and Env− backgrounds) was less than the those of the others (FIG. 1B, lanes 2 and 7; FIG. 2B, lanes 2 and 12), due to the lower levels of pgRNA-containing capsids formed by L60A in that experiment (FIG. 3; see below). The L95A and K96A mutants showed a pattern of (+)-strand DNA similar to that of the WT, including the presence of full-length (+)-strand DNA (FIG. 2), in agreement with the detection of mature rcDNA in the native DNA (FIG. 1). The lack of mature rcDNA in the native DNA, the L60A and I126A mutants showed only incomplete (+)-strand DNA and no full-length (+) strands (FIG. 2).

As mentioned above, the levels of core DNA in the L60A mutant were significantly lower in some cases than in the WT and the other mutants. We thus measured the RNA packaging levels of the WT and mutant core proteins. All of the core mutants assembled similar or higher levels of pgRNA-containing capsids compared to the WT, but the L60A mutant showed 2- to 3-fold-lower levels of pgRNA-containing capsids in Huh7 cells (FIG. 3B, lanes 2 and 7) and when expressed from the Env− background in HepG2 cells (FIG. 3A, lane 7) in the experiment shown. This decrease in pgRNA packaging could therefore account for the lower levels of core DNA in the L60A mutant observed above (FIGS. 1 and 2). The faster mobility of the K96A mutant (FIG. 3) was consistent with the loss of a positive charge contributed by K96 on the capsid surface, causing the mutant capsid to move faster toward the bottom (cationic) side of the agarose gel.

Example 2

Figure 4:
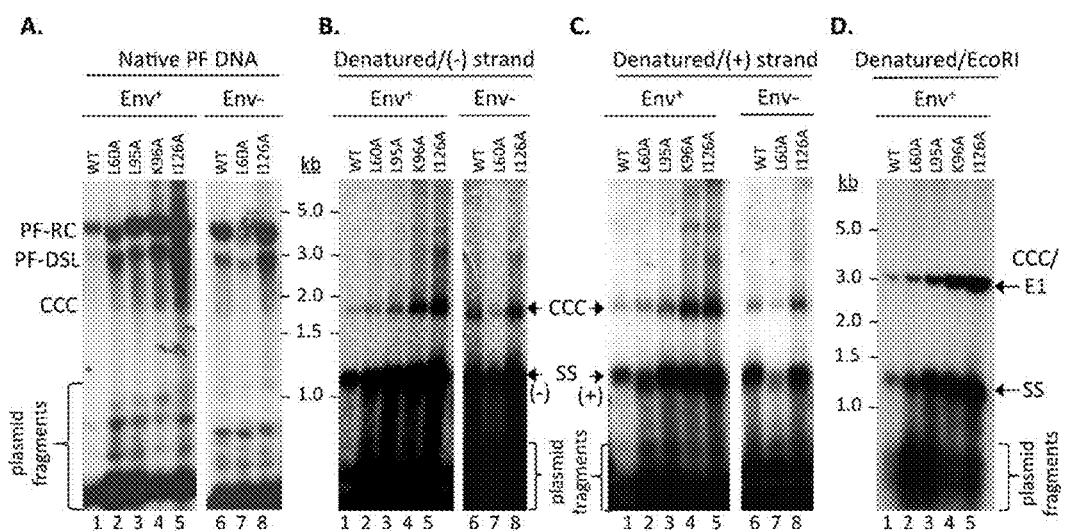
Figure 5:
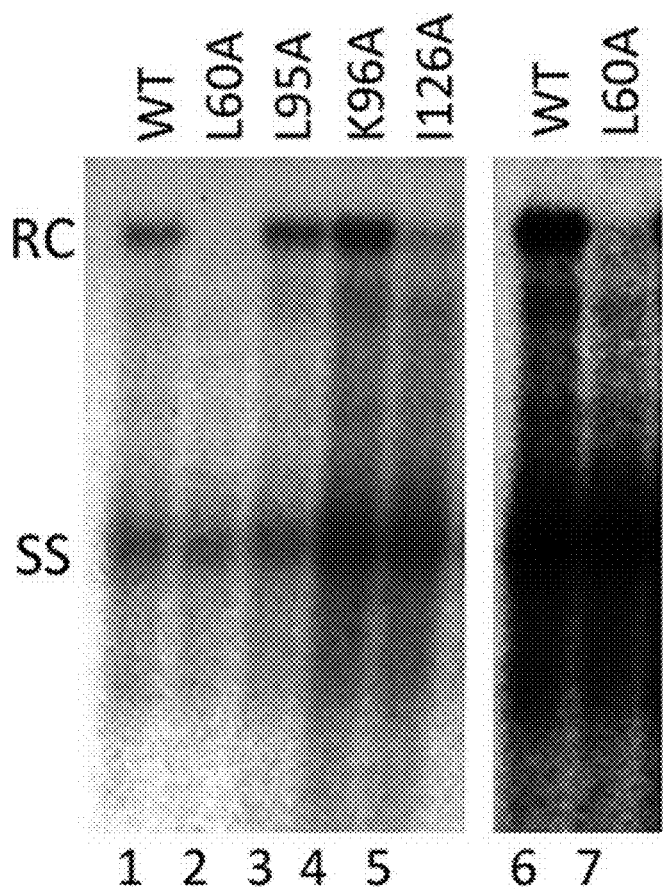

This Example demonstrates that the secretion-defective HBc mutants tested accumulated high levels of PF DNA, including cccDNA. In contrast to the apparent defect in core DNA accumulation described above, all core mutants tested were able to accumulate PF-RC (and PF-DSL) and cccDNA at levels similar to or higher than those of the WT in HepG2 cells (FIG. 4). The identity of the cccDNA was verified by heat denaturation (FIGS. 4B and C) and heat denaturation followed by linearization with the single-cutter restriction enzyme EcoRI (FIG. 4D), using a known approach (Gao W, Hu J. 2007. Formation of hepatitis B virus covalently closed circular DNA: removal of genome-linked protein. J Virol 81:6164-6174). In particular, even though the L60A and I126A mutants showed no rcDNA in NCs (FIG. 1), they showed abundant PF-rcDNA and cccDNA. Since no core rcDNA, the precursor to both the PF-RC and cccDNA, was detectable after the routine MNase digestion in the L60A and I126A mutants, the normalized PF-RC and cccDNA levels in these two mutants would be infinitely higher than those in the WT (Table 1). However, as described below, we were able to detect low levels of core rcDNA in the I126A mutant when the MNase digestion was omitted during core DNA extraction. Upon normalization to the low but detectable levels of this nuclease-sensitive core rcDNA in the I126A mutant, the PF-RC and cccDNA levels were 4.2- and 12.8-fold higher than those in the WT, respectively (Table 1). Similarly, very low levels of rcDNA were also detected in the L60A mutant NCs without the MNase digestion, which were even lower than those in the I126A mutant (FIG. 5 and Table 1). Upon normalization to the very small amounts of core rcDNA detected without the MNase digestion step, the PF-rcDNA and cccDNA levels in L60A were at least 3.6- and 3.9-fold higher than those in the WT, respectively (FIGS. 4A and B, lanes 2 and 7; Table 1). The K96A mutant, which accumulated mature rcDNA in contrast to the L60A and I126A mutants (FIG. 1), also showed higher levels (by 4- to 5-fold) of both PF-RC and cccDNA than the WT (Table 1), whereas the L95A mutant had levels of PF-rcDNA and cccDNA similar to those of the WT (Table 1). The presence or absence of the viral envelope proteins did not affect the pattern of the PF or core DNA from the L60A or I126A mutant (FIGS. 1 and 4 and Table 1). The apparently somewhat lower level of PF-RC and cccDNA from the L60A mutant (in the Env– background) compared to the WT (FIG. 4A to C, lane 7) could be accounted for by the smaller amount of pgRNA packaging and consequently lower core DNA levels (FIG. 1A, lanes 7 and 15, and 3A, lane 7).

The presence of full-length (+)-strand DNA, as well as full-length (–)-strand DNA, in the PF-rcDNA from the WT or all HBc mutants tested was further confirmed by its detection after denaturation of the PF-rcDNA (FIGS. 4B and C), in contrast to the absence of full-length (+) strands in the core DNA from the L60A and I126A mutants (FIGS. 2A and B, lanes 7 and 10). Also, essentially the same results were obtained in Huh7 cells, although the overall PF-RC and cccDNA levels by the WT and core mutants were lower than those in the HepG2 cells (data not shown).

Example 3

This Example demonstrates that the HBc mutants failed to protect rcDNA. The lack of rcDNA detection in NCs (FIG. 1) was apparently contradictory to the abundance of PF-RC and cccDNAs (FIG. 3) for the L60A and I126A mutants, since the PF-RC and cccDNAs are all derived from the core rcDNA following uncoating of mature NCs. One possibility that could account for this discrepancy was that these core mutants were in fact competent in making rcDNA, but mutant mature NCs containing the rcDNA were unstable and thus failed to accumulate. The instability of the mature NCs formed by the mutant core proteins, resulting in the disruption of the mutant mature NCs, could lead, on one hand, to enhanced uncoating resulting in a failure to accumulate mature NCs, as observed, and on the other, to rapid deproteination of rcDNA and cccDNA formation, accounting for the abundant levels of these DNA species shown for these mutants. Since an exogenous nuclease (MNase in this study) treatment was used, as is routine in the field, to remove input plasmids during the core DNA extraction shown in FIGS. 1 and 2 (see materials and methods described below), the putative unstable mature NCs formed by the mutant core proteins, which might have been accumulated in the cells, could have been eliminated as a result of the nuclease digestion. This possibility is consistent with the observation that certain capsid mutations of DHBV can indeed lead to preferential destabilization of mature NCs. To test this possibility, we extracted HBV core DNA in the absence of exogenous nuclease digestion of the cytoplasmic lysate. DpnI digestion was subsequently used to degrade the input plasmids (but not replicative viral DNA) from the purified core DNA.

As shown in FIG. 5, in the absence of MNase treatment, the levels of core rcDNA shown by the L95A and K96A core mutants were similar to those of the WT, just like the results obtained with core DNA extracted with MNase treatment (FIG. 1), indicating that these mutant capsids were able to protect the mature rcDNA like the WT capsids. Furthermore, significant amounts of core rcDNA were also detected in the I126A mutant, and low levels of rcDNA were detected in the L60A mutant (FIG. 5), despite the fact that no rcDNA was detected in cells transfected by these two core mutants when MNase was used to digest the lysate prior to viral DNA extraction. These results thus confirmed that at least some mature NCs were formed by the L60A and I126A mutants, but they failed to protect their rcDNA content. The failure of the mutant mature NC to protect its rcDNA content indicated a loss of structural integrity, which was consistent with its destabilization, but alternative interpretations remained possible. Upon normalization to the ssDNA levels, the levels of rcDNA in the I126A mutant were still ca. 3-fold lower than those of the WT, and those in the L60A mutant were at least 5-fold lower (Table 1). The fact that only very low levels of rcDNA were detected in the L60A mutant, even in the absence of MNase digestion, coupled with the detection of abundant levels of PF-rcDNA and cccDNA in this mutant further indicated that mature L60A NCs might be even more unstable than the I126A mutant NCs and that the mutant failed to accumulate significant amounts of mature NCs due to rapid uncoating.

Example 4

Figure 6:
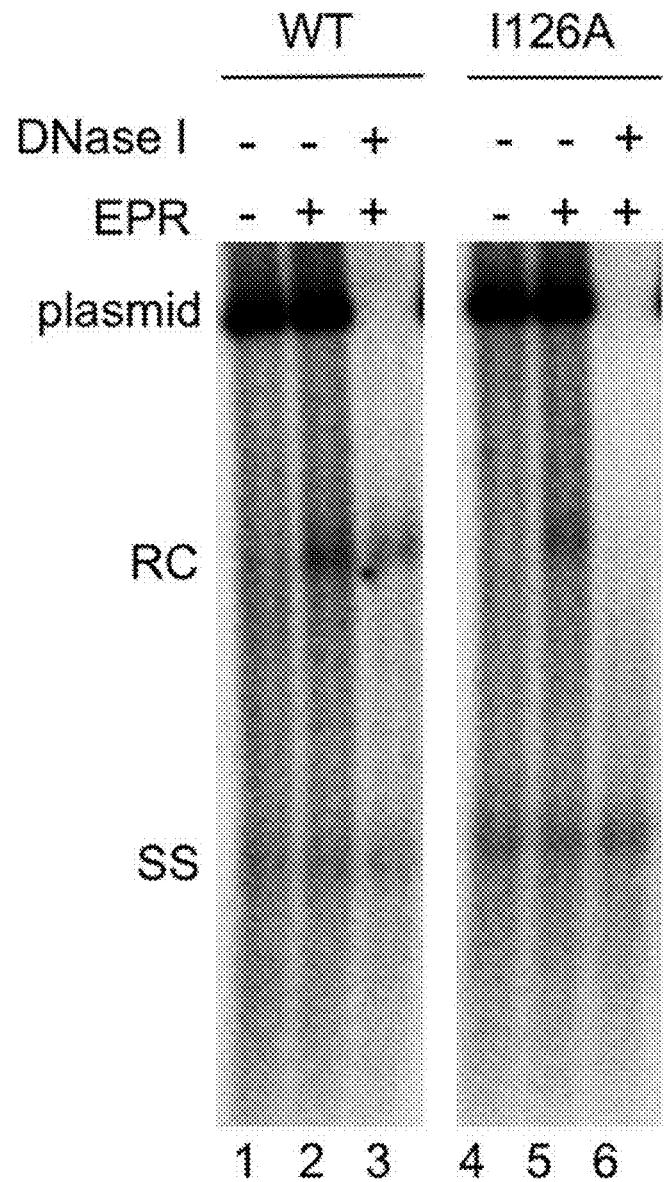

This Exampled demonstrates that I126A mutant NCs matured in vitro by EPR also failed to protect their rcDNA content. To test further the preferential instability induced by the I126A core mutation, we decided to make mature NCs in vitro using EPR. MNase digestion was used to eliminate all the mature NCs from the I126A mutant (and some WT mature NCs too) (30). The remaining (immature) NCs were then used for EPR to convert a portion of them to mature NCs, and the stability of the mature NCs made in vitro was tested by DNase I digestion (FIG. 6). The results showed that while a portion (ca. 30% or less) of mature WT NCs were unable to protect their rcDNA content, all mature I126A mutant NCs formed in vitro failed to protect their rcDNA. Thus, the I126A mature NCs formed in vitro, like those formed in vivo, lost their integrity. In contrast, ssDNA inside immature NCs was protected from DNase digestion by either the WT or I126A mutant NCs, as shown above.

Figure 7:
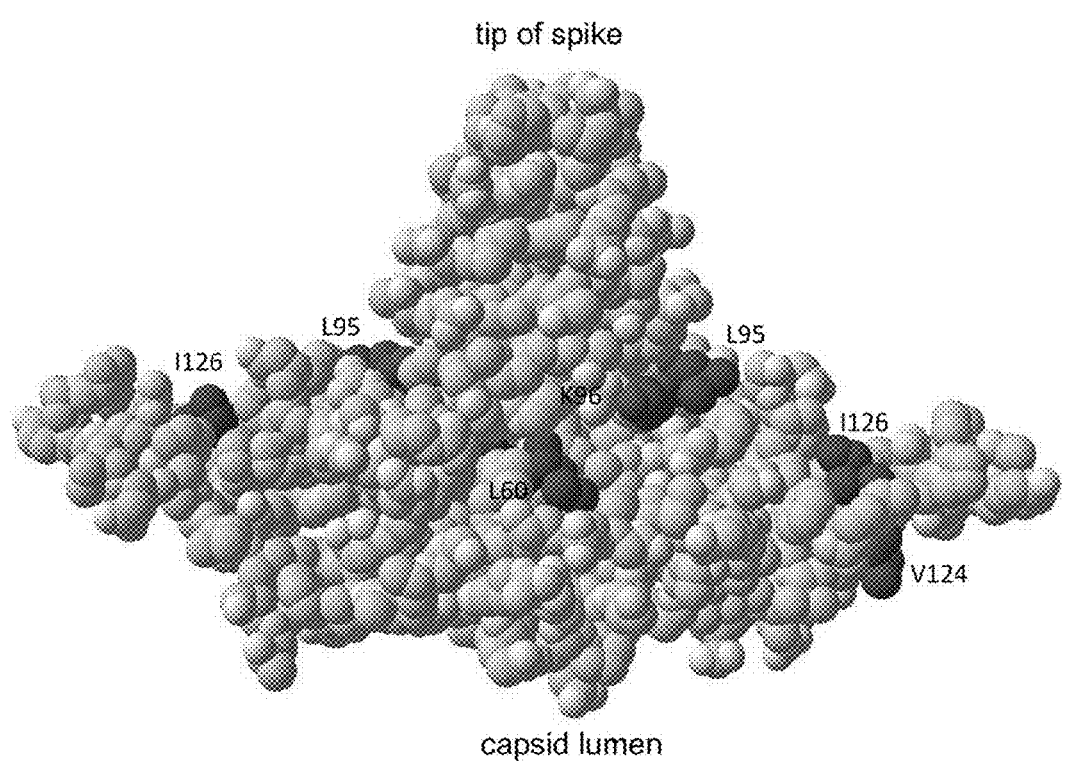

It will be apparent that the foregoing results demonstrate that the core NTD can significantly affect cccDNA levels. The effect of L60A and I126A on mature NC integrity suggests that these mutations likely increased cccDNA levels by enhancing NC uncoating and the release of rcDNA. On the other hand, the K96A mutation, which apparently did not significantly affect the integrity of the mature NCs, at least as measured here, still enhanced cccDNA levels. Among other possibilities, K96A mutation may instead affect the intracellular trafficking and nuclear import of the mature NC and its rcDNA content, prerequisites for cccDNA formation. Although only the core CTD is known to harbor nuclear localization signals (NLSs), it is possible that NTD could regulate the use of these NLSs in the CTD on the mature NC. Interestingly, the L95A mutation, right next to the K96A mutation, did not affect either NC integrity or cccDNA formation (FIG. 7).

All of the core NTD mutations tested here are located on the exterior surface of NCs (FIG. 7) and are defective in forming complete virions, indicating that the residues affected by these mutations are involved in mediating the interaction of mature NCs with the viral envelope proteins during virion formation. These residues may form part of the actual binding site on mature NCs that directly interacts with the viral envelope proteins. Thus, the mutations at positions 95 and 96, which showed no significant effect on NC integrity as measured here, may be part of a site that is directly recognized by the envelope proteins. Alternatively, the mutations at other sites (particularly L60 and I126) may affect NC-envelope interactions indirectly (e.g., by affecting the structural integrity of the mature NCs). In so doing, these mutations may interfere with the generation of the putative structural changes associated with NC maturation: i.e., with the emergence of the putative maturation signal that is recognized by the envelope proteins. On the other hand, all of these mutants remain competent for delivering rcDNA to the host cell nucleus for cccDNA formation. Thus, the determinants on the mature NC important for uncoating, nuclear import, and cccDNA formation can be separated genetically from those for its envelopment.

The two alternative fates of the mature HBV NC, nuclear import for cccDNA formation and envelopment for virion secretion, likely require that its stability be carefully regulated. If the mature NC is too stable, it will interfere with NC disassembly (uncoating). Thus, the preferential destabilization of mature NCs is most likely a reflection of the necessity to disassemble the mature NCs so their rcDNA content can be released into the host cell nucleus and is available for cccDNA formation. On the other hand, if the NC is too unstable, as suggested here for the L60A and I126A mutants, it may interfere with the maturation-associated structural changes required to trigger envelopment and virion secretion. Therapeutic manipulation of NC stability/integrity can thus potentially block cccDNA synthesis and/or virion secretion, thus highlighting the need for methods of this disclosure which is designed to enable discovery of agents suitable for that purpose.

Example 5

This Example provides a description of the materials and methods used to obtain the results described here.

Plasmids. DNA sequences encoding the wild-type (WT) and mutant HBc proteins were cloned from the pSVcore constructs (Ponsel D, Bruss V. 2003. Mapping of amino acid side chains on the surface of hepatitis B virus capsids required for envelopment and virion formation. J Virol 77:416-422) into pCMV-HBV/Env− (Gao W, Hu J. 2007. Formation of hepatitis B virus covalently closed circular DNA: removal of genome-linked protein. J Virol 81:6164-6174). A 345-bp BglII-BspEII fragment encoding HBc amino acid residues 30 to 144 from pSVcore, containing the WT sequences, or the L60A, L95A, K96A, I126A substitutions was used to replace the corresponding sequences in pCMV-HBV/Env−. To transfer the WT and mutant core coding sequences to the envelope-WT HBV constructs, a 1.6-kb SnaBI-EcoRI fragment containing the cytomegalovirus (CMV) promoter plus the coding sequences for the 5' third of pgRNA, encoding either the WT or mutant HBc proteins as described above, from pCMV-HBV/Env− was used to replace the CMV promoter and the 5' HBV sequences (until the unique EcoRI site) in pCIdA-HBV. The resulting pCIdA-HBV/pgRNA constructs direct the expression of the HBV pgRNA, expressing either WT or mutant HBc, under the CMV promoter and expression of the WT envelope proteins from the native HBV promoters.

Transient transfection. Transfection of HepG2 and Huh7 cells was done by adapting known approaches. Briefly, HepG2 cells in 60-mm dishes were transfected with 4 of plasmid using FuGENE6 (Promega). Huh7 cells seeded in 60-mm dishes were transfected with 10 μg of plasmid using the CalPhos mammalian transfection kit (Clontech). Cells were harvested on day 7 post-transfection for DNA analysis and the RNA packaging assay. EPR. NCs in 10 μl cytoplasmic lysate were pretreated with micrococcal nuclease (MNase [0.25 U/μl]) and CaCl2 (5 mM) at 37° C. for 1 h. The MNase was then inactivated by adding EGTA to 10 mM. The treated lysates were used in the endogenous polymerase reaction (EPR) by adapting known approaches. Briefly, the lysate was incubated with 100 μM each dATP, dGTP, dCTP, and TTP, an EDTA-free protease inhibitor cocktail (Roche), and the EPR buffer (50 mM Tris-HCl [pH 7.5], 10 mM MgCl2, 0.1% NP-40, 0.1% 2-mercaptoethanol) for 16 h at 37° C. for EPR in a final volume of 20 μl, whereby the viral RT packaged within NCs synthesizes DNA using the endogenous viral RNA and DNA templates packaged within the NCs. The DNA synthesized was then released by SDS-proteinase K digestion and detected by Southern blotting following agarose gel electrophoresis by adapting known methods.

Analysis of purified viral DNA. HBV core DNA (i.e., NC-associated DNA) and PF DNAs were isolated as previously described (Gao W, Hu J. 2007. Formation of hepatitis B virus covalently closed circular DNA: removal of genome-linked protein. J Virol 81:6164-6174), with minor modifications. Briefly, for isolation of core DNA, HepG2 or Huh7 cells were lysed in NP-40 lysis buffer. After removal of the nuclear pellet by brief centrifugation, the supernatant (cytoplasmic lysate) was incubated with MNase (150 U/ml) and CaCl2 (5 mM) at 37° C. for 90 min, and proteinase K was then used to digest viral DNA-protein complexes after NCs were precipitated with polyethylene glycol and disrupted by SDS. Viral core DNA was then purified by phenol-chloroform extraction and ethanol precipitation. PF DNA was isolated by Hirt extraction. Briefly, cells were lysed in SDS lysis buffer (50 mM Tris-HCl [pH 8.0], 10 mM EDTA, 150 mM NaCl, 1% SDS). The cell lysates were mixed with KCl and incubated at 4° C. overnight with gentle rotation. The lysate was then spun at 14,000×g for 20 min, and the supernatant was extracted three times with phenol and once with chloroform. The DNA was then recovered by ethanol precipitation. To isolate core DNA without MNase nuclease digestion, the MNase-CaCl2 treatment step was omitted, and DpnI digestion was used to remove plasmid DNA. DpnI digestion was also used to treat PF DNA to remove plasmid DNA (Gao W, Hu J. 2007. Formation of hepatitis B virus covalently closed circular DNA: removal of genome-linked protein. J Virol 81:6164-6174). Confirmation of cccDNA by heat denaturation and linearization by EcoRI digestion were performed as described before (Gao W, Hu J. 2007. Formation of hepatitis B virus covalently closed circular DNA: removal of genome-linked protein. J Virol 81:6164-6174). Purified core or PF DNA was analyzed by agarose gel electrophoresis and Southern blotting by adapting known techniques. Various viral DNA species were quantified by phosphorimaging or densitometry, and the signal of a particular DNA species from the HBc mutants was normalized first to that of the corresponding DNA species from the WT analyzed on the same gel. The normalized values were then used to calculate the ratios of the different DNA species shown in Table 1 Detection of NC-associated viral RNA (RNA packaging assay). Viral RNA packaging was analyzed by adapting known techniques. Briefly, intact NCs from MNase-digested cell lysate were analyzed by native agarose gel electrophoresis followed by detection using a 32P-labeled HBV plus-strand [(+)-strand]-specific riboprobe without the NaOH denaturation step prior to transfer to membrane. Under these conditions, we have shown previously that only pgRNA, but not (+)-strand DNA, in HBV NCs is detected (Hu J, et al. 2004. Requirement of heat shock protein 90 for human hepatitis B virus reverse transcriptase function. J Virol 78:13122-13131; Ning X, et al. Secretion of genome-free hepatitis B virus—single strand blocking model for virion morphogenesis of para-retrovirus. PLoS Pathog. 7:e1002255). The same membrane was subsequently probed with an anti-HBV core polyclonal antibody (Dako) to detect the core protein.

While the invention has been described through specific embodiments, routine modifications will be apparent to those skilled in the art and such modifications are intended to be within the scope of the present invention.

---

---

What is claimed is:

1. A method for identifying a candidate for use in reducing hepatitis B virus (HBV) in an individual, the method comprising:
    a) introducing at least one test agent into a mammalian cell culture comprising mammalian cells, the cells comprising one or more plasmids that encode an HBV genome, wherein the HBV genome comprises a segment encoding a mutated HBV core (HBc) protein, wherein the mutated core protein comprises an HBc mutation that is L60A, I126A, K96A or a combination thereof;
    b) allowing the test agent to be in contact with the mammalian cells, and subsequently,
    c) determining amounts of HBV covalently closed circular (ccc) DNA in the mammalian cells, wherein a reduction in cccDNA relative to a control indicates the at least one test agent is a candidate for reducing HBV in an individual.

2. The method of claim 1, wherein the mammalian cell culture is separated into a plurality of separate test containers, and wherein a different test agent is added into each test container.

3. The method of claim 1, wherein the control comprises a cccDNA value produced by a control mammalian cell culture comprising one or more plasmids that encode an HBV genome, wherein the genome comprises a segment encoding an HBV core (HBc) protein, wherein the encoded HBc protein does not comprise any of the mutations of claim 1.

4. The method of claim 2, wherein the plurality of test containers are comprised by a multi-well plate.

5. A method for screening test agents comprising:
    a) introducing into cells of a non-human mammalian subject a vector encoding an hepatitis B virus (HBV) genome, wherein the HBV genome comprises a segment encoding a mutated HBV core (HBc) protein, wherein mutated HBc protein comprises a mutation that is L60A, I126A, K96A, or a combination thereof;
    b) introducing into the mammalian subject a test agent, and subsequently
    c) determining amounts of HBV cccDNA in the mammal, wherein a reduction in the cccDNA relative to a control indicates the test agent is a candidate for use in reducing HBV in an individual.

6. The method of claim 5, wherein the control comprises a cccDNA value obtained from a non-human mammal comprising a vector encoding an HBV genome, wherein the genome comprises a segment encoding an HBV core (HBc) protein, wherein the encoded HBc protein does not comprise any of the mutations of claim 5.

7. A method for identifying an inhibitor of covalently closed circular (ccc) DNA production, the method comprising
   a) contacting a test agent with a mutated HBV core (HBc) protein comprising an HBc protein mutation that is L60A, I126A, K96A or a combination thereof, wherein the HBc protein is present in mammalian cells;
   b) allowing the test agent to be in contact with the HBc, and subsequently,
   c) determining conversion of relaxed circular (rc) rcDNA to cccDNA, wherein a reduction in conversion of rcDNA to cccDNA relative to a control identifies the test agent as an inhibitor of the cccDNA production.

8. The method of claim 7, wherein the control comprises a cccDNA value obtained from an HBc protein that does not comprise any of the mutations of claim 7.

\* \* \* \* \*